(12) United States Patent
Teague et al.

(10) Patent No.: US 7,559,934 B2
(45) Date of Patent: Jul. 14, 2009

(54) BEADED BASKET RETRIEVAL DEVICE

(75) Inventors: James A. Teague, Spencer, IN (US); Jason Kear, Bloomington, IN (US); Justin A. Reppert, Spencer, IN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 635 days.

(21) Appl. No.: 10/408,397

(22) Filed: Apr. 7, 2003

(65) Prior Publication Data

US 2004/0199200 A1    Oct. 7, 2004

(51) Int. Cl.
*A61B 19/00* (2006.01)
(52) U.S. Cl. .................................................. 606/113
(58) Field of Classification Search ............... 606/110, 606/113, 114, 108, 127, 200, 47, 49; 128/657, 128/772; 119/801, 802
See application file for complete search history.

(56) References Cited

U.S. PATENT DOCUMENTS

| | | | |
|---|---|---|---|
| 1,996,261 A | 4/1935 | Storz | |
| 2,556,783 A | 6/1951 | Wallace | |
| 3,137,298 A | 6/1964 | Glassman | |
| 3,472,230 A | 10/1969 | Fogarty | |
| 3,739,784 A | 6/1973 | Itoh | |
| 3,828,790 A | 8/1974 | Curtiss et al. | |
| 3,955,578 A | 5/1976 | Chamness et al. | |
| 4,046,149 A | 9/1977 | Komiya | |
| 4,046,150 A | 9/1977 | Schwartz et al. | |
| 4,198,960 A | 4/1980 | Utsugi | |
| 4,243,040 A | 1/1981 | Beecher | |
| 4,299,225 A | 11/1981 | Glassman | |
| 4,326,530 A | 4/1982 | Fleury, Jr. | |
| 4,347,846 A | 9/1982 | Dormia | |
| 4,425,908 A | 1/1984 | Simon | |
| 4,447,227 A | 5/1984 | Kotsanis | |
| 4,557,255 A | 12/1985 | Goodman | |
| 4,590,938 A | 5/1986 | Segura et al. | |
| 4,611,594 A | 9/1986 | Grayhack et al. | |
| 4,612,931 A | 9/1986 | Dormia | |
| 4,625,726 A | 12/1986 | Duthoy | |

(Continued)

FOREIGN PATENT DOCUMENTS

AU    56865/86    4/1986

(Continued)

OTHER PUBLICATIONS

PCT International Search Report for International Application No. PCT/US2004/007709, dated Aug. 13, 2004.

(Continued)

*Primary Examiner*—Anhtuan T. Nguyen
*Assistant Examiner*—Tuan V Nguyen
(74) *Attorney, Agent, or Firm*—Finnegan, Henderson, Farabow, Garrett & Dunner, LLP

(57) ABSTRACT

A medical retrieval device, and related method, for removing material (such as calculi and stones) from the body of a patient has the ability to capture and readily release material. The retrieval device includes a basket having at least one loop with first and second ends including a plurality of bead elements. The first end of the loop is immovable and the second end of the loop is slideably movable.

34 Claims, 10 Drawing Sheets

U.S. PATENT DOCUMENTS

| | | | |
|---|---|---|---|
| 4,650,466 A | 3/1987 | Luther | |
| 4,682,599 A | 7/1987 | Konomura | |
| 4,691,705 A | 9/1987 | Okada | |
| 4,699,147 A | 10/1987 | Chilson et al. | |
| 4,706,671 A | 11/1987 | Weinrib | |
| 4,718,419 A | 1/1988 | Okada | |
| 4,723,549 A | 2/1988 | Wholey et al. | |
| 4,728,319 A | 3/1988 | Masch | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,893,621 A | 1/1990 | Heyman | |
| 4,907,572 A | 3/1990 | Borodulin et al. | |
| 4,926,858 A | 5/1990 | Gifford, III et al. | |
| 4,927,426 A | 5/1990 | Dretler | |
| 4,927,427 A | 5/1990 | Kriauciunas et al. | |
| 4,994,079 A | 2/1991 | Genese et al. | |
| 4,998,539 A | 3/1991 | Delsanti | |
| 5,011,488 A | 4/1991 | Ginsburg | |
| 5,030,201 A | 7/1991 | Palestrant | |
| 5,041,093 A | 8/1991 | Chu | |
| 5,053,008 A | 10/1991 | Bajaj | |
| 5,057,114 A | 10/1991 | Wittich et al. | |
| 5,064,428 A | 11/1991 | Cope et al. | |
| 5,071,407 A | 12/1991 | Termin et al. | |
| 5,084,054 A | 1/1992 | Bencini et al. | |
| 5,100,423 A | 3/1992 | Fearnot | |
| 5,102,415 A | 4/1992 | Guenther et al. | |
| 5,122,147 A | 6/1992 | Sewell | |
| 5,171,233 A | 12/1992 | Amplatz et al. | |
| 5,176,688 A | 1/1993 | Narayan et al. | |
| 5,192,286 A | 3/1993 | Phan et al. | |
| 5,255,679 A | 10/1993 | Imran | |
| 5,290,294 A | 3/1994 | Cox et al. | |
| 5,311,858 A | 5/1994 | Adair | |
| 5,329,942 A | 7/1994 | Gunther et al. | |
| 5,330,482 A | 7/1994 | Gibbs et al. | |
| 5,345,936 A | 9/1994 | Pomeranz et al. | |
| 5,354,310 A | 10/1994 | Garnic et al. | |
| 5,372,124 A | 12/1994 | Takayama et al. | |
| 5,374,273 A | 12/1994 | Nakao et al. | |
| 5,376,100 A | 12/1994 | Lefebvre | |
| 5,421,832 A | 6/1995 | Lefebvre | |
| 5,437,646 A * | 8/1995 | Hunt et al. | 604/167.04 |
| 5,471,982 A | 12/1995 | Edwards et al. | |
| 5,476,450 A | 12/1995 | Ruggio | |
| 5,484,402 A | 1/1996 | Saravia et al. | |
| 5,486,183 A | 1/1996 | Middleman et al. | |
| 5,496,330 A | 3/1996 | Bates et al. | |
| 5,499,981 A | 3/1996 | Kordis | |
| 5,522,819 A * | 6/1996 | Graves et al. | 606/113 |
| 5,549,626 A | 8/1996 | Miller et al. | |
| 5,562,678 A | 10/1996 | Booker | |
| 5,588,952 A | 12/1996 | Dandolu | |
| 5,599,299 A | 2/1997 | Weaver et al. | |
| 5,607,420 A | 3/1997 | Schuman | |
| 5,658,296 A | 8/1997 | Bates et al. | |
| 5,693,069 A | 12/1997 | Shallman | |
| 5,891,153 A | 4/1999 | Peteson | |
| 5,944,728 A | 8/1999 | Bates | |
| 6,024,738 A * | 2/2000 | Daikuzono et al. | 606/7 |
| 6,059,793 A | 5/2000 | Pagedas | |
| 6,083,220 A | 7/2000 | Guglielmi et al. | |
| 6,096,053 A | 8/2000 | Bates | |
| 6,152,932 A | 11/2000 | Ternström | |
| 6,159,220 A | 12/2000 | Gobron et al. | |
| 6,174,318 B1 * | 1/2001 | Bates et al. | 606/127 |
| 6,187,017 B1 * | 2/2001 | Gregory, Jr. | 606/127 |
| 6,224,612 B1 | 5/2001 | Bates et al. | |
| 6,248,117 B1 * | 6/2001 | Blatter | 606/153 |
| 6,264,664 B1 | 7/2001 | Avellanet | |
| 6,319,262 B1 | 11/2001 | Bates et al. | |
| 6,575,988 B2 * | 6/2003 | Rousseau | 606/151 |
| 7,101,379 B2 * | 9/2006 | Gregory et al. | 606/127 |
| 2001/0041899 A1 * | 11/2001 | Foster | 606/127 |
| 2002/0173804 A1 | 11/2002 | Rousseau | |
| 2003/0225419 A1 * | 12/2003 | Lippitt et al. | 606/127 |
| 2004/0030375 A1 | 2/2004 | Pierce | |

FOREIGN PATENT DOCUMENTS

| | | |
|---|---|---|
| DE | 2804058 A1 | 8/1978 |
| DE | 3213223 A1 | 10/1983 |
| DE | 3407708 A1 | 9/1985 |
| DE | 3522649 A1 | 1/1986 |
| DE | 8707515 U1 | 9/1987 |
| DE | 8707516 U1 | 10/1987 |
| DE | 3620385 C1 | 1/1988 |
| DE | 3633527 A1 | 4/1988 |
| DE | 4025799 A1 | 2/1992 |
| EP | 0160870 A2 | 11/1985 |
| EP | 0160870 A3 | 11/1985 |
| EP | 0160870 B1 | 11/1985 |
| EP | 0 195 444 | 9/1986 |
| EP | 0 195 444 A2 | 9/1986 |
| EP | 0 428 998 A1 | 5/1991 |
| EP | 0 737 450 A1 | 10/1996 |
| FR | 2694687 A1 | 2/1994 |
| GB | 2 020 557 A | 11/1979 |
| JP | 3-205043 | 9/1991 |
| WO | 91/11209 | 8/1991 |
| WO | 92/05828 | 4/1992 |
| WO | 92/16153 | 10/1992 |
| WO | 93/15671 | 8/1993 |
| WO | 94/24946 | 11/1994 |
| WO | 95/05129 | 2/1995 |
| WO | 96/01591 | 1/1996 |
| WO | 99/48429 | 12/1999 |
| WO | 00/71036 A2 | 11/2000 |
| WO | 01/10290 A2 | 2/2001 |

OTHER PUBLICATIONS

Vorwerk et al., "Percutaneous Embolectomy: In Vitro Investigations of the Self-expanding Tulip Sheath", Radiology, (1992) 182:415-418.

Vorwerk et al., "Percutaneous Balloon Embolectomy with a Self-expanding Tulip Sheath: In Vitro Experiments", Radiology (1995) 197:153-156.

* cited by examiner

BEADED BASKET RETRIEVAL DEVICE

TECHNICAL FIELD

The invention relates generally to surgical retrieval devices for removing biological or foreign material from the body. More particularly, the invention relates to medical retrieval devices for capturing and releasing material such as stones from a body lumen.

BACKGROUND INFORMATION

Medical retrieval devices generally are used to retrieve biological and foreign material from the body including stones. Such medical retrieval devices include, for example, retrieval baskets, and may be used through an endoscope or a laparoscope.

One type of known device has a sheath and a retrieval assembly such as a basket that is movable in and out of the sheath. When the basket is within the sheath, the basket assumes a collapsed, reduced diameter profile. When the sheath is retracted relative to the basket or the basket is moved beyond the end of the sheath, the basket expands to a relatively larger diameter than when the basket is enclosed within the sheath. Generally, the contour of known baskets is round or oval and is formed by a plurality of legs.

With many known retrieval devices, it is technically difficult to release captured material such as a stone from the retrieval assembly once the stone is captured. In some patients, a cicatrix, for example, or some other constriction that reduces the diameter of the lumen of the tract may form in the tract in which the stone is lodged because of recurrent trauma caused by the stone to the lining of the tract. The narrowed lumen of the tract may not be so narrow so as to interfere with insertion of a retrieval device while the retrieval device is in a collapsed position. However, after the retrieval device is inserted into the tract, the retrieval assembly expanded, and the stone captured within the device, the diameter of the retrieval assembly containing the stone may exceed the inner diameter of the narrowed lumen of the tract or the inner diameter of the orifice of the tract into which the retrieval device is inserted. If an excessive pulling force is used by the operator in an attempt to remove the retrieval device and stone, the retrieval device may traumatize the orifice or the lining of the tract or, worse, perforate the tract. In addition, the retrieval device may assume an everted configuration causing damage upon being withdrawn from the tract. Under these conditions, the stone must first be released from the retrieval device followed by withdrawal of the collapsed retrieval device from the tract. If the stone can not be released from the retrieval device, more invasive, surgical approaches are required to disengage the stone from the retrieval device and to remove the retrieval device from the body tract.

With most, if not all, current medical retrieval device designs, it is difficult to disengage the stone or other material from the retrieval assembly so that the retrieval device can be collapsed and then removed from the body. A medical retrieval device that is capable of collapsing to release a stone captured by the device in the body of a patient is needed. The device described herein addresses this need.

SUMMARY OF THE INVENTION

In general, the invention described herein provides a medical retrieval device including an assembly, such as a retrieval basket for capturing material in the body of a patient and optionally releasing the material in the patient's body. The retrieval device according to the invention can be used in urological, hepatobiliary, cardiovascular or endoscopic applications by procedures that are minimally invasive. The medical retrieval device described herein may be manufactured from materials that are substantially resistant to the energy emitted from holmium lasers. In a specific application of the device according to the invention, the retrieval device can be used for capturing stones within a body tract such as the biliary or urinary tract.

In general, in one aspect, the invention features a medical retrieval device comprising at least one loop including a plurality of beads. The loop has a first end and a second end. The first end of the loop is immovable and the second end of the loop is slideably moveable. The slideable movement of the second end of the loop moves the loop for capturing the material in the body of the patient.

The medical device can include a sheath having a distal portion, a proximal portion, and defining a lumen.

The loop of the medical device can have at least two positions, a retracted position wherein the loop is constrained within the lumen of the sheath, and a deployed position wherein the loop is extended beyond the distal portion of the sheath. The deployed position of the medical retrieval device may have a deployed expanded position wherein the loop is expanded and a deployed collapsed position wherein the loop is deployed and collapsed.

The beads can be manufactured from nitinol, polymers, ceramics, stainless steel, or any combination thereof. The plurality of beads can be made from a material substantially resistant to laser energy. The beads can be sized and configured to be self-aligning when the loop including the beads is pulled taut. In a particular embodiment according to the invention, each of the beads has a lumen and each of the loops of the medical retrieval device include a wire that is slideably moveable within the lumen of each of the beads. An elongated member may be connected to the immovable first end of the loop. In a particular embodiment according to the invention, the medical retrieval device includes two loops and a distal tip that links together the two loops.

Another aspect of the invention features a system for retrieving material from a body comprising an elongated member having a distal end, a proximal end, and a basket. The basket is disposed at the distal end of the elongated member and has a plurality of N legs formed by N/2 loops. The loops have a first end and a second end. The first end of the loop is fixed, for example, to the distal end of the elongated member, and the second end of the loop is moveable. The loops include a plurality of beads having a lumen with a portion of the plurality of N legs extending therethrough. In a particular embodiment according to the invention, the basket has a retracted position in which the basket is positioned in the lumen of the sheath, a deployed position in which the basket is positioned beyond the distal portion of the sheath and open, and a collapsed position in which the basket is positioned beyond the distal portion of the sheath and the plurality of N legs are collapsed.

In one embodiment, the system can have a distal tip linking the distal ends of the loops. The beads can be sized and configured to form a basket of predetermined size when the basket is in the extended position. The system can include a handle having a first actuator for moving the basket between the retracted and deployed positions.

In another aspect, the invention relates to a method for retrieving biological or foreign material from a body, comprising the steps of (a) providing a device which includes (i) an elongated member including a distal end and a proximal end; (ii) a basket disposed at the distal end of the elongated member, the basket having a plurality of N legs formed by N/2 loops; and (iii) a plurality of beads having a lumen with a portion of one of the plurality of N legs extending therethrough defining the loops; (b) inserting the device into the body of a patient; (c) capturing the material with the basket; and (d) withdrawing device from the body to remove the material from the body.

The step of capturing the material can include capturing a calculus, a kidney stone, a ureteral stone, a bladder stone, or a stone in the biliary tree.

Another aspect of the invention features a medical retrieval device having a basket including at least one loop including a wire and a plurality of beads, each of the beads further comprising a lumen for slideably receiving the wire of the loop. In a particular embodiment of this aspect of the invention, the wire of the loop may have a first end and a second end, the first end being slideably moveable and the second end being immovable.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

The embodiments described herein have features in common including a retrieval basket having at least one loop having a plurality of beads, which in a proper configuration form the basic shape of the basket. The retrieval basket of the invention is used to retrieve one or more stones and/or other calculi, objects, or other material from a body tract such as biliary and pancreatic ducts, hepatic ducts, cystic duct, common bile duct, ureters, urinary bladder, urethra, renal pelvis, and kidney.

Figure 1:
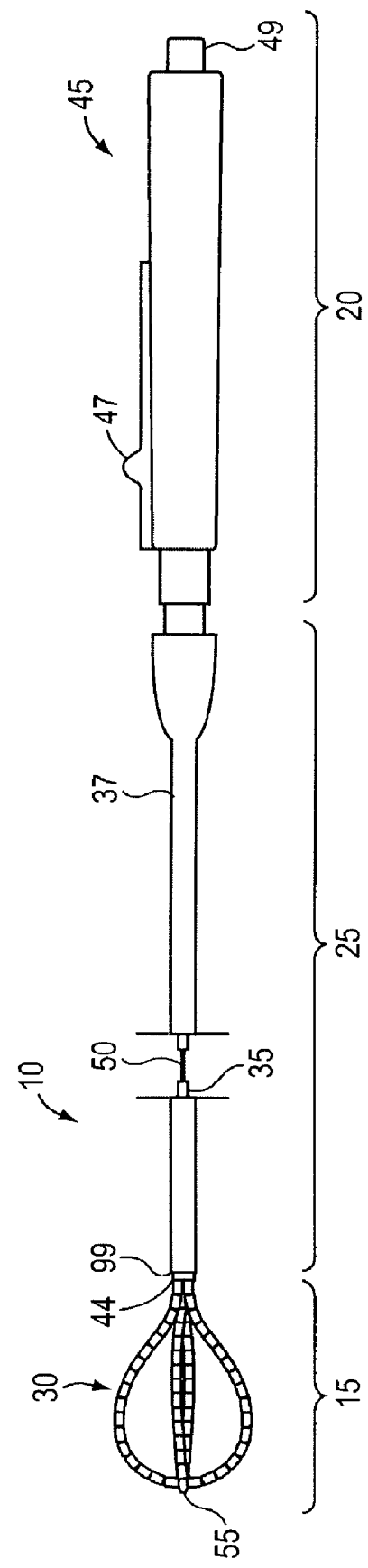
FIG. 1 illustrates a side view of one embodiment of a medical retrieval device with the basket in open position according to the invention.

Referring to FIG. 1, one embodiment of the retrieval device 10 is shown according to the invention. The retrieval device 10 includes a distal portion 15, a proximal portion 20, and an intermediate portion 25 therebetween. A basket 30 is located at the distal portion 15, an elongated member 35 extends along the intermediate portion 25, and a proximal handle 45 is located at the proximal portion 20. The elongated member 35 is joined to a basket base 44 at the distal end of the elongated member 35, and to the handle 45 at the proximal end of the elongated member 35. In one embodiment of the invention, the elongated member 35 includes a central lumen 40 longitudinally disposed in the elongated member 35. A sheath 37 defining a lumen 39 extends from the handle 45 to the distal portion 15 of the retrieval device 10.

Figure 2A:
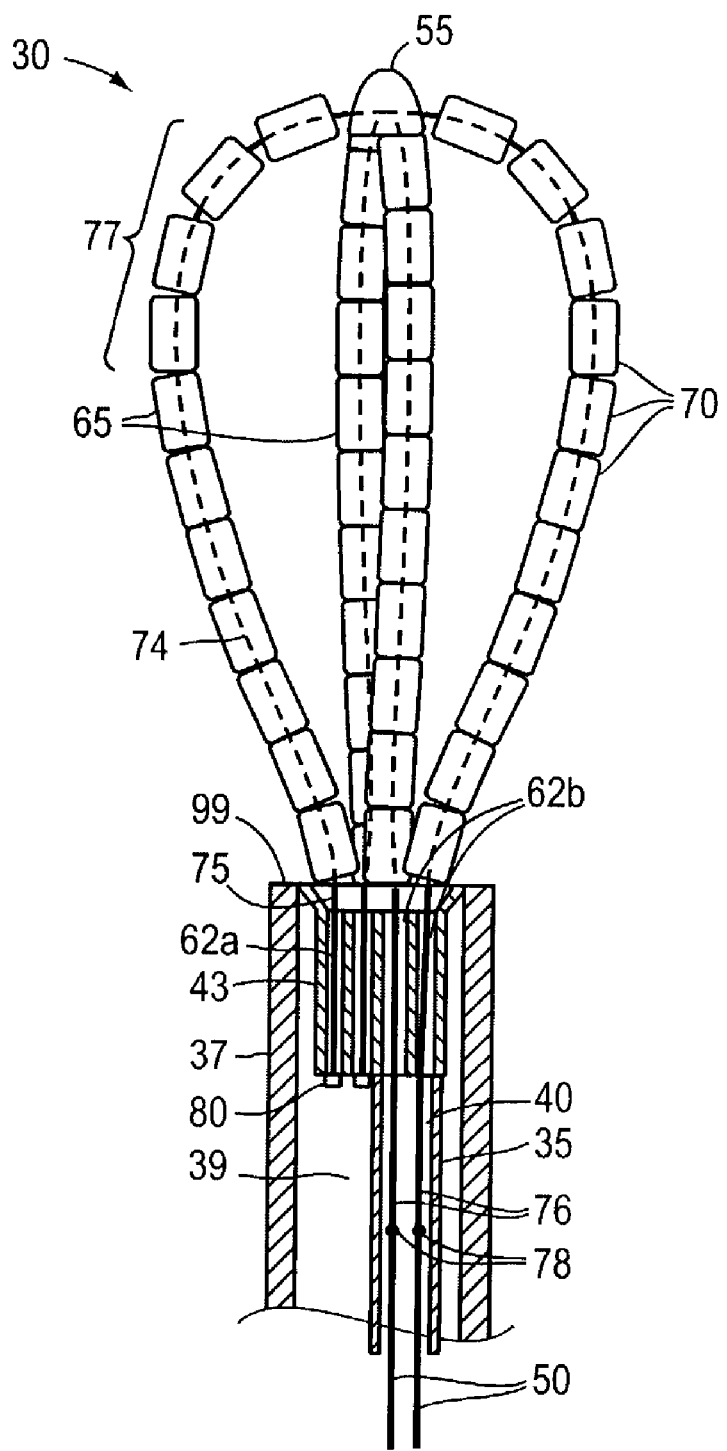
FIG. 2A illustrates a detailed view of the basket of the medical retrieval device in the deployed position according to one embodiment of the invention.

Referring now to FIG. 2A, the elongated member 35 is longitudinally disposed and slideably moveable in the lumen 39 of the sheath 37. Sheath 37 is preferably made of commonly available materials which provide sufficient strength and flexibility for adequate operation, but which are soft enough to avoid trauma or irritation to the body lumen in which the sheath 37 is deployed. Materials which may be used to form the sheath 37 include biocompatible polyethylenes, nylons, PEBAX (Ato Chimie Corporation, Allee des Vosges Courbevoie, France), TEFLON (E. I. du Pont de Nemours and Company, Wilmington, Del.), urethane, silicones, other suitable polymer materials, and combinations of the aforementioned materials.

Referring again to FIG. 1, in one embodiment, the proximal handle 45 includes a first actuator 47 and a second actuator 49. At least one of the actuators 47, 49 is disposed within the proximal handle 45 and connected to one or more basket connecting lines 50. The one or more basket connecting lines 50 are disposed and slideably moveable in the lumen 39 of the sheath 37 or, alternatively, in the lumen 40 of the elongated member 35.

In one embodiment, with continued reference to FIG. 2A, basket connecting lines 50 are slideably moveable within the central lumen 40 of the elongated member 35. The basket connecting lines 50 are attached to the basket 30 at the distal portion 15 and are attached to the proximal handle 45 (not shown) at the proximal portion 20. The basket 30 includes a basket tip 55 at a distal end and the basket base 43 at a proximal end of the basket 30. A cuff 44 is disposed around the basket base 43.

Figure 2B:
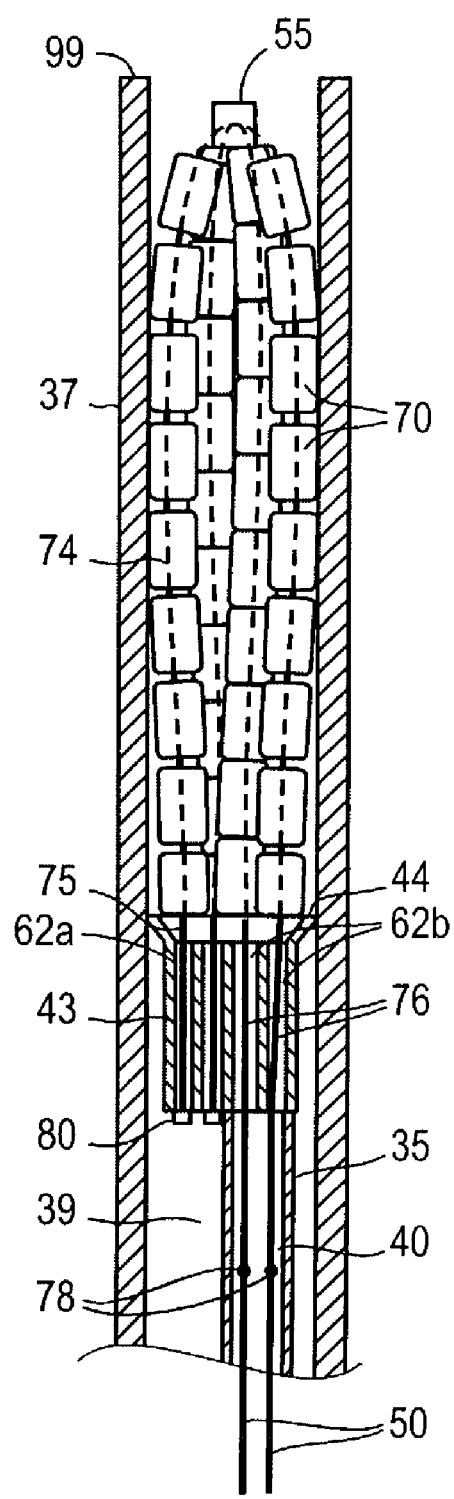
FIG. 2B illustrates a detailed view of the basket of the medical retrieval device in the retracted position according to one embodiment of the invention.

The basket 30 is slideably positionable relative to a distal end 99 of the sheath 37. For example, in one embodiment according to the invention, the basket 30 can be fixed in a stationary position with the sheath 37 operably joined to one of the actuators 47, 49 and slideably moveable in a first direction to deploy and open the basket 30 as illustrated in FIG. 2A, and in a second direction to retract and constrain the basket 30 within the lumen 39 of the sheath 37 as illustrated in FIG. 2B. In an alternative embodiment, the sheath 37 is in a fixed position and the elongated member 35 is operably joined to one of the actuators 47, 49 and is slideably moveable in a first direction within the lumen 39 of the sheath 37 to deploy and open the basket 30 and in a second direction to cover and collapse the basket 30 within the lumen 39 of the sheath 37.

With renewed reference to FIG. 2A, the basket 30 further includes one or more loops 65 which extend between the basket tip 55 and the basket base 43 to form the shape of the basket 30. The basket base 43 is disposed at the distal end of the elongated member 35. The basket tip 55 and the basket base 43 define the respective distal and proximal portions of the basket 30. In one embodiment according to the invention, the basket is defined by a plurality of legs 77 formed by the loops 65. For N legs 77, there are N/2 loops 65. For example, a basket 30 having two legs 77 contains one loop 65, a basket 30 having four legs 77 contains two loops 65, a basket 30 having six legs 77 contains three loops 65, and so on. Other configurations of the basket 30 are contemplated by the invention.

With continued reference to FIG. 2A in one embodiment according to the invention, the basket base 43 has a plurality of lumens 62a, 62b. Alternatively, the basket base 43 may have only one lumen 62. Each loop 65 includes a plurality of beads 70 each bead having a lumen 73. The beads 70 are strung together along a wire 74 extending through the lumen 73 disposed in each of the beads 70. A first end 75 of the wire 74 is disposed through a lumen 62a of the basket base 43 and attached at a wire attachment point 80, or alternatively attached to the distal end of the elongated member 35.

Figure 2C:
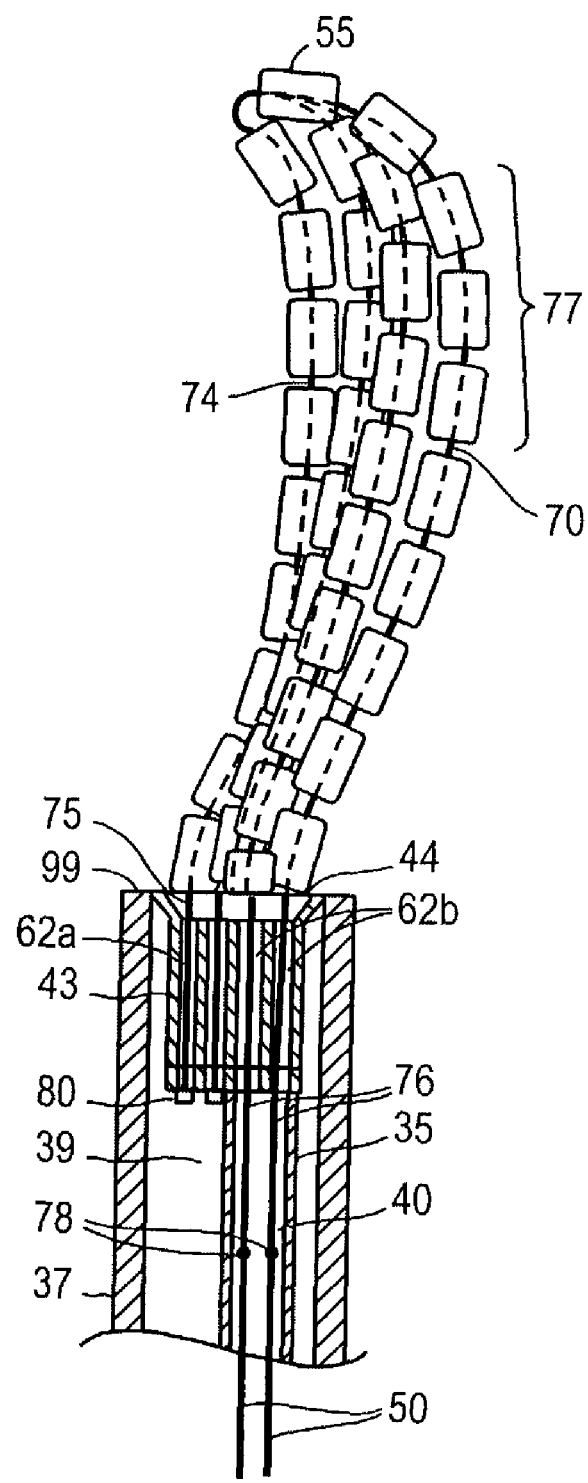
FIG. 2C illustrates a detailed view of the basket of the medical retrieval device in the deployed and collapsed position according to one embodiment of the invention.

Referring still to FIG. 2A in one embodiment according to the invention, the basket base 43 includes a cuff 44 through which the wire 74 passes. The basket cuff 44 is interposed between the basket base 43 and the beads 70. A second end 76 of the wire 74 is slideably disposed through a lumen 62b of the basket base 43 and is attached to the distal end 78 of the basket connecting line 50. The lumen 62b of the basket base 43 is sized with a diameter large enough to allow slideable movement of the second end of the wire 76 and yet small enough to prevent passage of the beads 70 through the basket base 43 (and basket cuff 44, if so included). Accordingly, when tension is applied to the basket connecting line 50 to make the basket connecting line 50 taut, the beads 70 of the loop 65 are compressed together along the wire 74 and against the basket base 43 and the basket shape is formed as shown in FIG. 2A. When the connecting line 50 is released to relax the connecting line 50, the beads 70 separate from one another and the basket 30 collapsed as illustrated in FIG. 2C.

Figure 3:
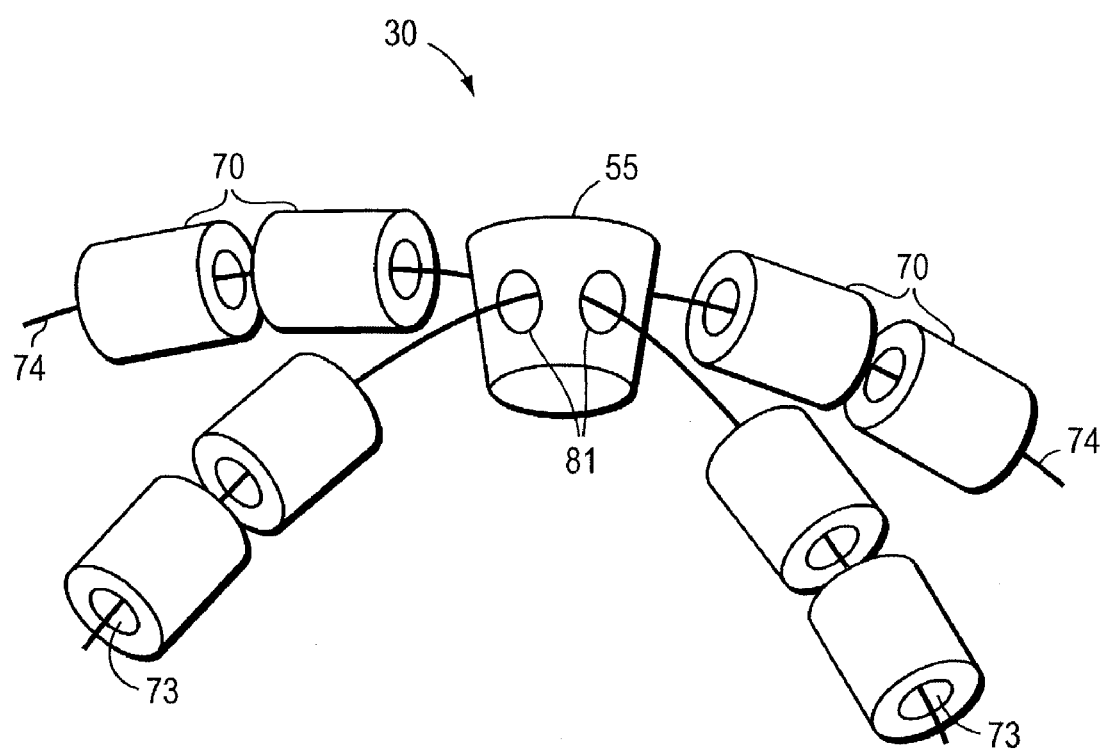
FIG. 3 illustrates a detailed view of the basket tip and the interface with the basket beads according to one embodiment of the invention.
Figure 4A:
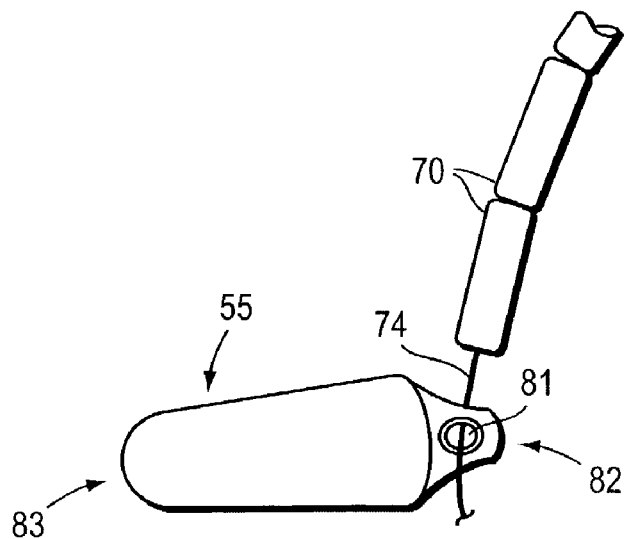
FIG. 4A to 4D illustrate detailed views of the basket tip located at the distal end of the medical retrieval device according to one embodiment of the invention.
Figure 4B:
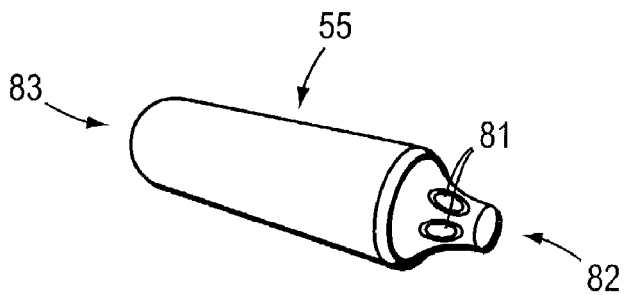
Figure 4C:
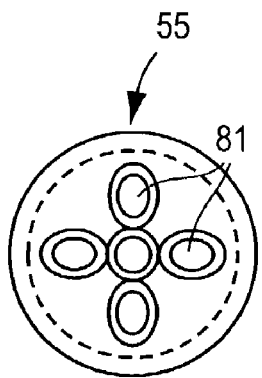
Figure 4D:
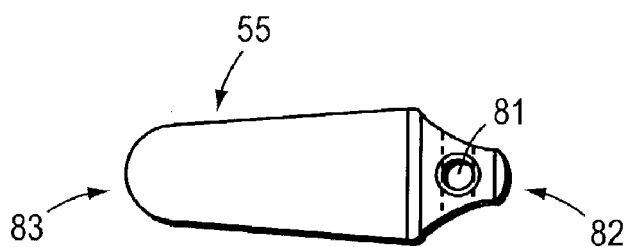

Referring now to FIG. 3, the distal end of the basket 30 includes one or more wires 74 that are threaded through the basket tip 55 and the lumen 73 of each of the plurality of beads 70 to form the loops 65 that make the basket 30. In one embodiment, for example, shown in FIGS. 4A and 4B, the wire 74 extends through wire aperture 81 disposed through a proximal portion 82 of the basket tip 55. As shown in FIG. 4B, a distal portion 83 of the basket tip 55 is tapered or frusto-conical in shape to provide atraumatic passage through a body lumen. Referring to FIG. 4C, in one embodiment according to the invention, the basket tip 55 may have a plurality of apertures 81 to receive one or more wires 74. Referring to FIG. 4B in one embodiment, for example, four wire apertures 81 may be disposed within the basket tip 55. This arrangement of apertures 81 is suitable for two wires 74 (a pair of apertures for each wire 74). Three or more wires 74 are also contemplated, requiring six of more wire apertures 81, accordingly. The basket tip 55 can be shaped to provide ease of insertion and passage through a body lumen. The portion of the basket tip 55 interfacing with the other beads 70 of the loops 65 (FIG. 4A) can be shaped to modify the basket shape when the connecting line 50 and wire 74 is pulled taut as illustrated in FIG. 2A.

In one embodiment, the beads 70 are made of a thermoplastic, polymeric or ceramic material that is substantially resistant to holmium laser energy. Alternatively, the beads 70 can be made of a metal such as nitinol, stainless steel, or any combination of the aforementioned materials. The wire 74 can be made from a suture material. In one preferred embodiment, the wire 74 is a nitinol core with a polytetrafluoroethylene (PTFE) outer coating.

Figure 5A:
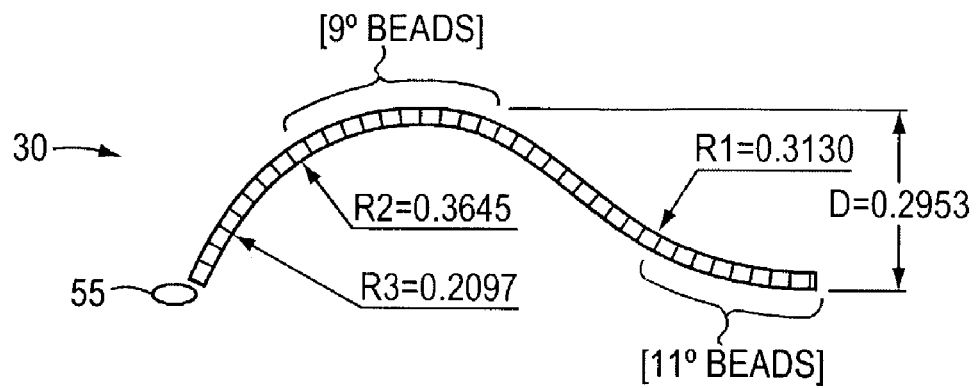
FIGS. 5A to 5C illustrate detailed views of the bead elements of the basket located at the distal end of the medical retrieval device according to one embodiment of the invention.
Figure 5B:
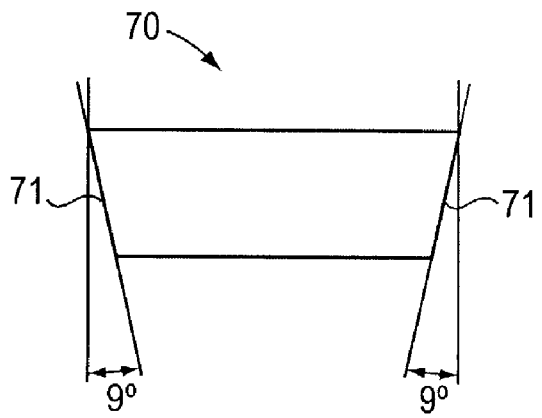
Figure 5C:
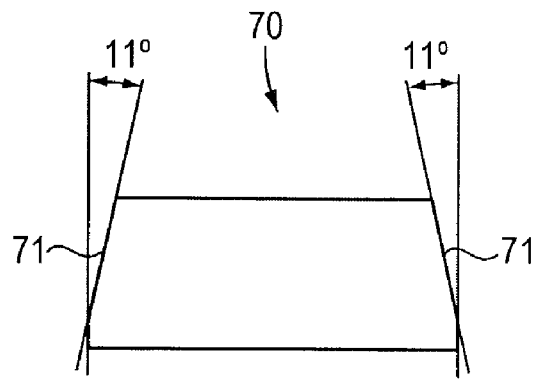

Referring now to FIGS. 5A-5C, the beads 70 of the loop 65 can be formed into specific shapes, particularly at the mating surfaces 71 between the beads 70, so that the beads are self-aligning in that the shape of the basket 30 is formed when tension is applied to the connecting line 50 and the wire 74 that runs through the lumen 73 of each of the beads 70. The beads 70 of the device 10 are each any suitable pierced member for forming the basket 30. The beads may comprise a variety of shapes, including, for example, cylindrical, spherical, ellipsoidal, toroidal, parallelapipedal, and cubical.

Referring to FIG. 5A, in one particular embodiment, the profile geometry of the basket 30 may include beads 70 of the loop 65 having mating surfaces 71 that are canted at various angles to form a basket 30 of desired configuration. In one particular embodiment, two kinds of beads 70 are used: a 9-degree bead whereby the mating surfaces 71 at each end of the bead 70 is canted 9 degrees from the vertical as shown in FIG. 5B; and an 11-degree bead whereby the mating surfaces 71 at each end of the bead 70 is canted 11 degrees from the vertical as shown in FIG. 5C. The beads 70 may be canted at other angles at one or both ends of the bead 70 and/or the bead 70 may also be curved along the longitudinal axis of the bead 70 (not shown). For example, the radii of the basket 30 defining the configuration illustrated in FIG. 5A, is shown with R1 equal to measured 0.3130 inches, R2 equal to 0.3645 inches, and R3 equal to 0.2097 inches. The distance, D from the basket base equals 0.2953 inches. Other basket configurations and dimensions including other radii are contemplated by the invention.

The beads 70 can also include surface characteristics for specific applications. For example, in one embodiment, the beads 70 can be textured to enhance the material gripping properties. All or a portion of the surface of any of the beads 70 can be roughened by a variety of means including, but not limited to, applying a material coating, forming teeth or ribs on the bead surface, or etching the bead surface.

Figure 6A:
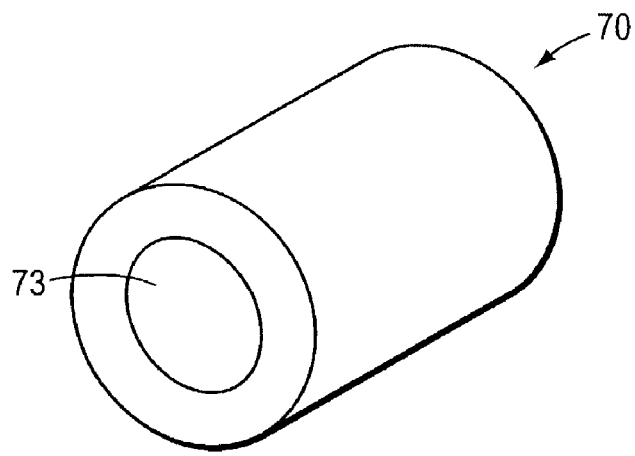
FIG. 6A illustrates a perspective view of one of the bead elements of the distal end of the medical retrieval device according to one embodiment of the invention.
Figure 6D:
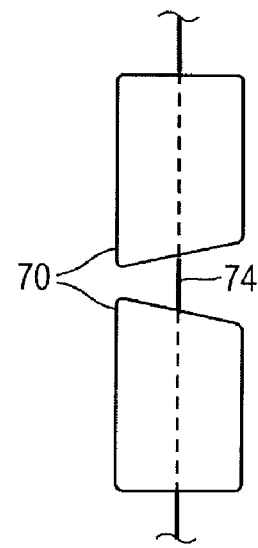
FIG. 6D illustrates a side view of two bead elements in a loose configuration.
Figure 6B:
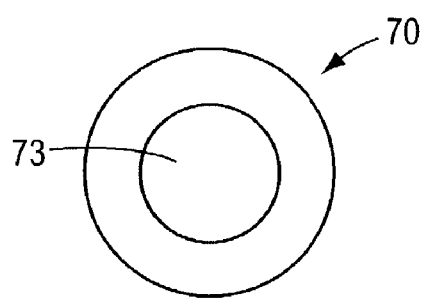
FIG. 6B illustrates a side view of one of the bead elements of the distal end of the medical retrieval device according to one embodiment of the invention.
Figure 6C:
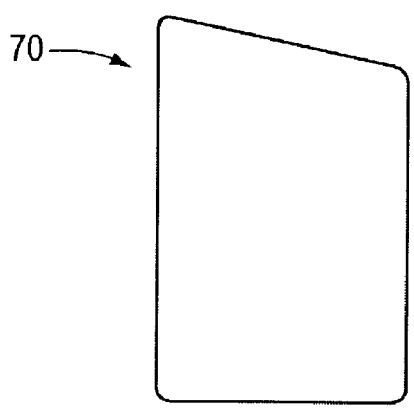
FIG. 6C illustrates an end view of one of the bead elements of the distal end of the medical retrieval device according to one embodiment of the invention.
Figure 6E:
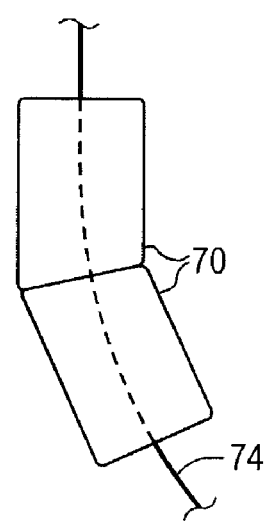
FIG. 6E illustrates a side view of two bead elements in coupled configuration.

Referring to FIGS. 6A and 6B, the diameter of the lumen 73 of the beads 70 is sized at least with a diameter sufficient to allow the wire 74 to slideably move through the lumen 73. As shown in FIGS. 6C-6E in one embodiment, the mating surfaces 71 may be angled to effect the shape of the basket 30 when the wire 74 is pulled taut. In other embodiments, the mating surfaces 71 of the beads 70 can be adapted for specific use or application to modify the basket into other desired shapes when tension is applied to the wire 74.

Figure 7A:
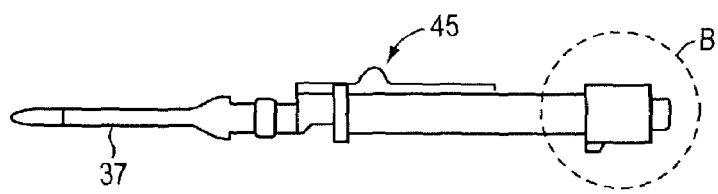
FIG. 7A illustrates a side view of the actuator located at the proximal end of the medical retrieval device according to one embodiment of the invention.
Figure 7B:
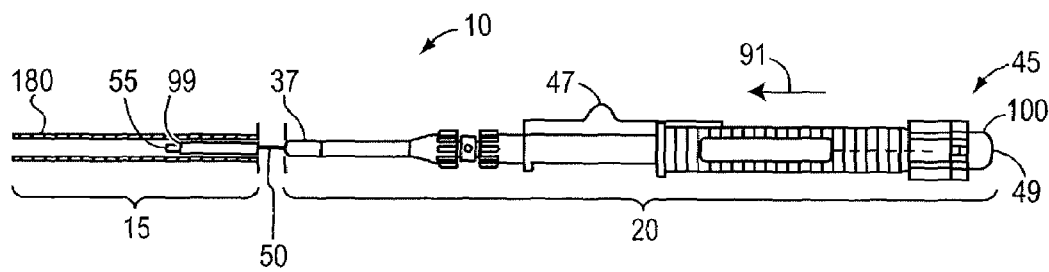
FIG. 7B illustrates a side view of the medical retrieval device in a clinical application with the basket in the retracted position according to one embodiment of the invention.
Figure 7C:
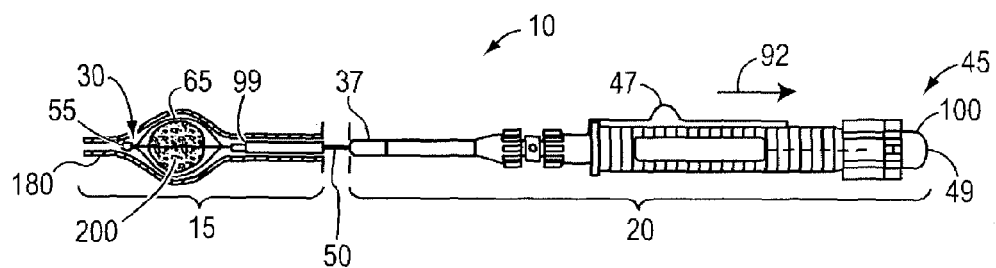
FIG. 7C illustrates a side view of the medical retrieval device in a clinical application with the basket in the deployed position and coupling a calculus, according to one embodiment of the invention.

Referring now to FIG. 7A, in one embodiment, the first actuator 47 is similar to the actuator described in U.S. Pat. No. 5,944,728, co-owned with the present application, the entire contents of which are hereby incorporated by reference. Slideably moving the first actuator 47 in a distal direction towards the distal end of the sheath 37 indicated by arrow 91 (FIG. 7B) causes the sheath 37 to cover and constrain the basket 30 within the sheath lumen 39 as shown in FIG. 7B. Conversely, slideably moving the first actuator 47 in a proximal direction towards the operator indicated by arrow 92 (FIG. 7C) causes the sheath 37 to retract from the basket 30 as shown in FIG. 7C. The loops 65 of the basket 30 are biased in an outwardly radial direction such that the loops 65 spring outward when the sheath 37 is withdrawn from the basket 30 deploying the basket 30 from the distal end 99 of the sheath 37, the loops 65 assuming an arcuate shape, thereby forming basket 30 as shown in FIG. 7C.

Figure 7D:
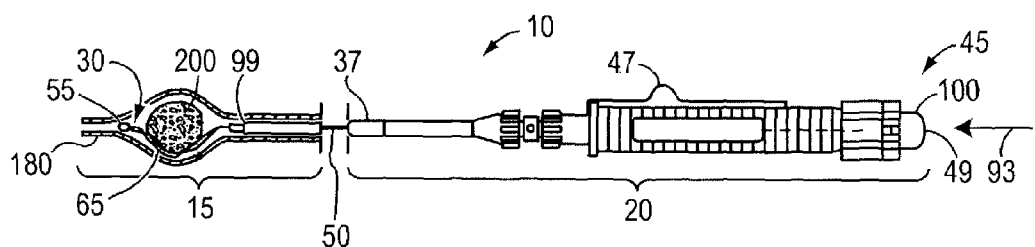
FIG. 7D illustrates a side view of the medical retrieval device in a clinical application with the basket in the deployed and collapsed position and releasing a calculus, according to one embodiment of the invention.

Once the first actuator 47 positions the basket 30 in the deployed and opened position illustrated in FIG. 7C, the second actuator 49 can collapse the basket 30 as illustrated in FIG. 7D, without retracting the basket 30 into the sheath 37.

Figure 8A:
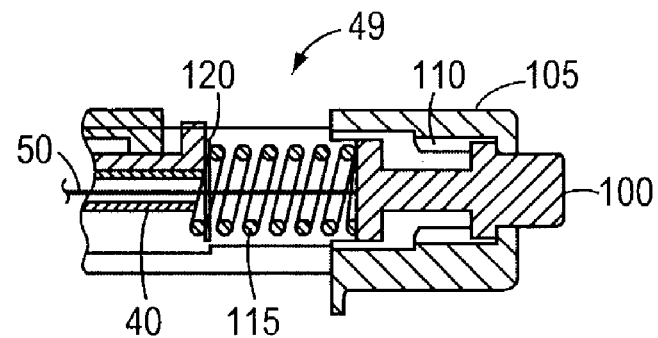
FIG. 8A illustrates a detailed view of one embodiment of the actuator at the proximal end of the medical retrieval device according to one embodiment of the invention.

Referring to FIG. 8A, a sectional view of the second actuator 49, identified by area B of FIG. 7A is depicted. The second actuator is disposed within the proximal handle 45. In the embodiment shown in FIG. 8A, the second actuator 49 includes a thumb button 100 slideably disposed and retained by an outer cap 105. The outer cap 105 is affixed to the proximal end of the proximal handle 45. The thumb button 100 slides within the retaining slots 110 of the outer cap 105. The thumb button 100 is biased in a proximal direction by a spring tensioner 115, the spring tensioner 115 is disposed between a spring plate 120 and the thumb button 100. One or more basket connecting lines 50 extend from the basket 30 at the distal portion 15 of the device 10 through the central lumen 40 of the elongated member 35, or, alternatively, through the lumen 39 of the sheath 37, through the proximal handle 45, and through the spring tensioner 115 for attachment to the thumb button 100.

Referring still to FIG. 8A, pushing the thumb button 100 compresses the spring tensioner 115 between the button 100 and the spring plate 120 and moves the basket connecting line 50 in a distal direction to substantially reduce the tension in the wire 74 of each of the loops 65 in the basket 30. This, in turn, collapses the basket 30 as illustrated in FIG. 8C, and permits release of captured material. This release capability is applicable in instances requiring immediate and unexpected removal of the device 10 from the body. Releasing the thumb button 100 permits the spring tensioner 115 to restore tension to the basket connecting line 50, the wire 74, and the loops 65, thereby re-forming the expanded basket shape of the basket 30 as illustrated in FIG. 7C. Although only a single basket connecting line 50 is shown in FIG. 7C for clarity, multiple connection lines 50 corresponding to multiple loops 65 of the basket 30 are contemplated.

Figure 8B:
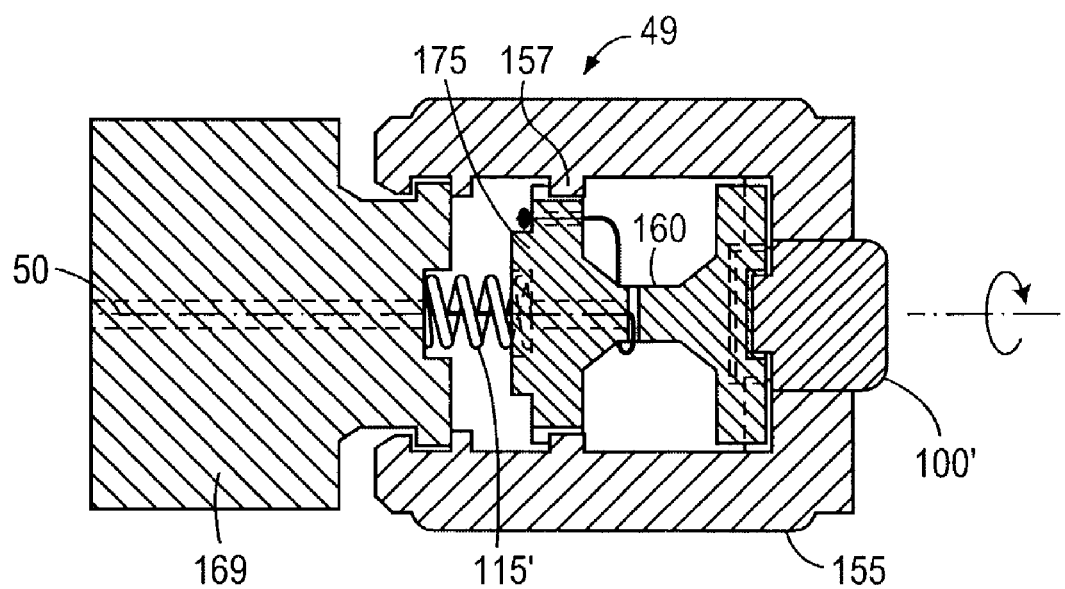
FIG. 8B illustrates a detailed view of another embodiment of the actuator at the proximal end of the medical retrieval device according to one embodiment of the invention.

In an alternative embodiment, the second actuator 49 can be configured as shown in FIG. 8B. A thumb button 100' is disposed through an outer cap 155 and is coupled to an inner spool 160. The inner spool 160 is slideably disposed within the outer cap 155, and engages an actuator cam 157 attached to outer cap 155. The inner spool 160 is affixed to the outer cap 155, therefore rotating the outer cap 155 causes rotation of the inner spool 160. The inner spool 160 is biased in a proximal direction by a spring tensioner 165. The spring tensioner 165 is longitudinally compressed between a mandrel 169 and the inner spool 160. The basket connecting line 50 is threaded through a bore in the mandrel 170, the spring tensioner 165, and around the inner spool 160 and finally the connecting line 50 terminates at the wire attachment point 175 disposed on the inner spool 160. Depressing the thumb button 150 compresses the spring tensioner 165 between the mandrel 169 and the inner spool 160, and moves the basket connecting line 50 in a distal direction to substantially reduce the tension in the wire 74 of each of the loops 65 in the basket 30. This in turn collapses the basket 30 and permits the release of the captured material. Fully depressing the thumb button 150 causes the inner spool 160 to engage the actuator cam 157 and releasably lock the thumb button 150 in the depressed position and the basket 30 in the open and collapsed position.

With the thumb button 150 locked in the depressed position, the operator can rotate the outer cap 155 in a first direction, thereby rotating the inner spool 160 in a first direction. The rotation of the inner spool 160 winds the basket connecting line 50 onto the inner spool 160 and advances the connecting line 50 in a proximal direction to increase the compressive force of the basket 30. This allows the operator to set a threshold retention force for retaining the captured material or to apply sufficient force to the material captured within the basket 30 for fragmentation of the stone. The operator can rotate the outer cap 155 in a second direction, opposite the first direction, which in turn rotates the inner spool 160 in an opposite direction and unwinds the basket connecting line 50 from the inner spool 160. This advanced the connecting line 50 in a distal direction and allows the basket 30 to collapse and open. With this arrangement, the second actuator 49 can be locked at one or more positions to secure the basket 30 in an open state, a closed state, or various positions therebetween in one of two ways. This configurations allows the operator to tighten the basket connecting lines 50 with varying force, permitting the operator to selectively set the compressive strength of the basket 30 for retrieving and retaining material from the body.

As shown in FIG. 7B, an operator (e.g., a physician) introduces the device 10 into a body tract 180 of the patient with the basket 30 retracted into the lumen 39 of the sheath 37 at its distal end 99 to achieve the retracted position. In one embodiment, the operator can then position the distal portion 15 of the retrieval device 10 proximate to the material to be retrieved such as, for example, a kidney stone, a ureteral stone, urethral stone, a bladder stone, a gallbladder stone, cholelith, or bile duct stone. As schematically depicted in FIG. 7C, the operator moves the first actuator 47 in the direction of the arrow 92 to withdraw the sheath 37 from the basket 30 to fully deploy the basket 30 from the lumen 39 of the sheath 37 into a deployed expanded position. With the basket 30 fully deployed from the lumen 39, the basket loops 65 extend radially and the basket 30 becomes sized and configured into a shape, for example, as illustrated in FIG. 7C, that can be manipulated over the material to be retrieved (e.g., a calculus 200).

Referring to FIG. 7C, once the operator positions the basket loops 65 generally around the material, the material can be captured within the basket 30 for subsequent removal from the body or the operator can readily release the material should the anatomical environment require it. By now advancing the sheath 37 over the basket 30 in the direction of the arrow 91 (FIG. 7B), the device may also serve as a mechanical lithotripsy system for crushing or fragmenting stones that are too large to removed intact from the body tract 180 by compressing the stone within the basket 30.

A situation can arise during the course of a clinical procedure performed by the operator where ready release of the captured material from the basket 30 is required to permit removal of the device 10 from the patient. Referring now to FIG. 7D, in one embodiment, after capture of the material in the body and while the basket 30 is in the deployed expanded position extending from the end of the sheath 37, the captured material (such as calculus 200) can be released from the basket 30, by depressing the thumb button 100 of the second actuator 49 to rapidly release tension from the basket connecting lines 50 thereby collapsing the basket 30 into a deployed collapsed position and releasing the material disposed within the basket 30. To restore the loops 65 to the previous radially outward position (illustrated in FIG. 7C, the operator releases the thumb button 100 thereby returning tension to the basket connecting lines 50 and the wire 74 of the loops 65. Accordingly, referring again to FIG. 2A, the beads 75 strung along the wire 74 of each loop 65 are compressed together between the basket tip 55 and the basket cuff 44 of the basket 30. The mating surfaces 71 of the beads 75 are configured to from a basket 30 having a predetermined size and shape.

In general, the basket, elongated member 35, and proximal handle 45 are not necessarily shown in their correct size or proportion to each other. The size of the basket 30 and elongated member 35 are dimensioned for the application of the retrieval device in the body. For example, for most biliary type applications, the total working length of the distal portion 15 and the intermediate portion 25 ranges from about 60 inches (150 cm) to about 120 inches (300 cm), and preferably about 71 inches (180 cm). In one embodiment, the size of the basket 30 and elongated member 35 are dimensioned for use within a 3.2 mm or larger diameter working channel of an endoscope. In one embodiment, the length of the beads 70 ranges from 0.040 inches (1 mm) to 0.197 inches (5 mm), the outer diameter of the beads 70 can range from 0.006 inches (0.152 mm) to 0.015 inches (0.381 mm), and the inner diameter of the beads 70 can range from 0.004 inches (0.102 mm) to 0.006 inches (0.152 mm).

The invention can be embodied in other specific forms without departing from the spirit or essential characteristics thereof. Therefore, it must be expressly understood that the foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A medical retrieval device for capturing material in the body of a patient, comprising:
   at least two loops, each of the at least two loops comprising a plurality of beads, a first end, and a second end,
   the first end of at least one loop being fixed and the second end of the at least one loop being slideably moveable relative to the first end, slideable movement of the second end of the at least one loop moving the at least one loop for capturing material in the body of the patient;
   a tapered distal tip linking the at least two loops, the at least one loop being slideably moveable relative to the tip,
   the tip having a proximal-most end and a side surface extending distally therefrom, the side surface defining a plurality of apertures;
   a sheath having a distal portion, a proximal portion, and defining a lumen; and
   wherein the at least two loops comprise two positions, a retracted position wherein the loops are constrained within the lumen of the sheath, and a deployed position wherein the loops are extended beyond the distal portion of the sheath, and the deployed position comprises a deployed expanded position wherein the loops are expanded, and a deployed collapsed position wherein the loops are collapsed.

2. The medical retrieval device of claim 1 wherein the plurality of beads comprise a material substantially resistant to laser energy.

3. The medical retrieval device of claim 1 wherein the plurality of beads comprise at least one of nitinol, stainless steel, a polymer, and a ceramic.

4. The medical retrieval device of claim 1 wherein the plurality of beads are sized and configured to be self-aligning when the loop is pulled taut.

5. The medical retrieval device of claim 1 wherein each bead comprises a lumen.

6. The medical retrieval device of claim 5 wherein the at least two loops further comprise a wire wherein the wire is slideably moveable within the lumen of each bead.

7. The medical retrieval device of claim 1 further comprising an elongated member connected to the fixed first end of the at least one loop.

8. The medical retrieval device of claim 1, wherein the first end of each loop of the at least two loops is fixed.

9. The medical retrieval device of claim 1, wherein the second end of each loop of the at least two loops is slideably moveable relative to the first end.

10. The medical retrieval device of claim 9, wherein the second end of each loop is independently moveable.

11. The medical retrieval device of claim 1, wherein the first end of the at least one loop is fixed relative to a base of the device disposed proximal the tip.

12. The medical retrieval device of claim 1, wherein each loop of the at least two loops is independently slideably moveable relative to the tip.

13. The medical retrieval device of claim 1, wherein the tip defines at least one lumen.

14. The medical retrieval device of claim 13, wherein a portion of the at least one loop is disposed within the at least one lumen of the tip.

15. The medical retrieval device of claim 1, wherein the tip has a different shape than at least one bead of the plurality of beads.

16. The medical retrieval device of claim 1, wherein a distal end of the tip defines a diameter greater than a diameter of the proximal-most end of the tip.

17. The medical retrieval device of claim 1, wherein the side surface is shaped to mate with a surface of an adjacent bead of the plurality of beads.

18. The medical retrieval device of claim 1, wherein the tip further includes a first surface extending distally from the side surface and angled from the side surface.

19. The medical retrieval device of claim 1, wherein the plurality of apertures share a central axis, the central axis being transverse to a longitudinal axis of the device.

20. The medical retrieval device of claim 1, the tip further including a rounded distal end.

21. The medical retrieval device of claim 1, the tip further including a distal portion extending beyond a distal-most portion of the at least two loops.

22. A system for retrieving material from a body, the system comprising:
   an elongated member comprising a distal end, and a proximal end;

a basket disposed at the distal end of the elongated member, the basket comprising a plurality of legs formed by at least two loops, each of the at least two loops comprising a first end and a second end, the first end of at least one loop being fixed and the second end of the at least one loop being slideably moveable relative to the first end;

a tapered distal tip linking the at least two loops, the at least one loop being slideably moveable relative to the tip, the tip having a proximal-most end and a side surface extending distally therefrom, the side surface defining a plurality of apertures;

a plurality of beads having a lumen with a portion of one of the plurality of legs extending therethrough;

a sheath having a lumen, wherein the basket has a retracted position in which the basket is positioned in the lumen of the sheath, a deployed position in which the basket is positioned beyond the distal portion of the sheath and open, and a collapsed position in which the basket is extended beyond the distal portion of the sheath and the plurality of legs are collapsed;

a proximal handle including a first actuator and a second actuator, the first actuator moveable relative to the second actuator to move the basket and sheath relative to one another between the retracted position and deployed position; and the second actuator moveable relative to the first actuator to move the basket between the deployed position and the collapsed position.

23. The system according to claim 22 wherein the plurality of beads are sized and configured to form a basket of predetermined size when the basket is in the deployed position.

24. The system according to claim 22 wherein the first end of the at least one loop is fixed to the distal end of the elongated member.

25. The system of claim 22 further comprising a means for selectively setting tension to the at least one loop.

26. The system of claim 22, wherein the first end of each loop of the at least two loops is fixed.

27. The system of claim 22, wherein the second end of each loop of the at least two loops is slideably moveable relative to the first end.

28. The system of claim 27, wherein the second end of each loop is independently moveable.

29. The system of claim 22, wherein the first end of the at least one loop is fixed relative to a base of the basket.

30. The system of claim 22, wherein each loop of the at least two loops is independently slideably moveable relative to the tip.

31. The system of claim 22, wherein the tip defines at least one lumen.

32. The system of claim 31, wherein a portion of the at least one loop is disposed within the at least one lumen of the tip.

33. The system of claim 22, wherein the tip has a different shape than at least one bead of the plurality of beads.

34. The system of claim 22, wherein the plurality of apertures share a central axis, the central axis being transverse to a longitudinal axis of the device.

\* \* \* \* \*